US011028350B2

(12) United States Patent
Mueller et al.

(10) Patent No.: US 11,028,350 B2
(45) Date of Patent: Jun. 8, 2021

(54) POWDERS AND GRANULES AND PROCESS FOR MAKING SUCH POWDERS AND GRANULES

(71) Applicant: BASF SE, Ludwigshafen am Rhein (DE)

(72) Inventors: Michael Klemens Mueller, Ludwigshafen (DE); Armin Stamm, Ludwigshafen (DE); Frank Jaekel, Ludwigshafen (DE); Carsten Sueling, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 106 days.

(21) Appl. No.: 16/309,339

(22) PCT Filed: Jun. 1, 2017

(86) PCT No.: PCT/EP2017/063285
§ 371 (c)(1),
(2) Date: Dec. 12, 2018

(87) PCT Pub. No.: WO2017/220308
PCT Pub. Date: Dec. 28, 2017

(65) Prior Publication Data
US 2019/0119611 A1 Apr. 25, 2019

(30) Foreign Application Priority Data

Jun. 20, 2016 (EP) ..................... 16175240
Apr. 24, 2017 (EP) ..................... 17167683

(51) Int. Cl.
| | | |
|---|---|---|
| *C11D 7/26* | (2006.01) | |
| *C11D 7/32* | (2006.01) | |
| *C11D 11/00* | (2006.01) | |
| *C11D 3/33* | (2006.01) | |
| *C11D 11/02* | (2006.01) | |
| *C07C 229/16* | (2006.01) | |
| *C07C 227/00* | (2006.01) | |
| *C07C 227/44* | (2006.01) | |
| *C11D 3/37* | (2006.01) | |

(52) U.S. Cl.
CPC ........ *C11D 11/0082* (2013.01); *C07C 227/00* (2013.01); *C07C 227/44* (2013.01); *C07C 229/16* (2013.01); *C11D 3/33* (2013.01); *C11D 3/3757* (2013.01); *C11D 11/0064* (2013.01); *C11D 11/02* (2013.01)

(58) Field of Classification Search
CPC ...... C11D 3/33; C11D 3/3757; C11D 11/0064
USPC ...................... 510/476, 480, 499
See application file for complete search history.

(56) References Cited

U.S. PATENT DOCUMENTS

| | | |
|---|---|---|
| 6,462,006 B1 | 10/2002 | Sorg et al. |
| 2011/0054215 A1 | 3/2011 | Euser et al. |
| 2012/0149936 A1 | 6/2012 | Baranyai |
| 2012/0202731 A1 | 8/2012 | Mrzena et al. |
| 2013/0284210 A1 | 10/2013 | Hueffer et al. |
| 2015/0353475 A1 | 12/2015 | Doppen et al. |
| 2016/0221930 A1 | 8/2016 | Baranyai |
| 2017/0058239 A1 | 3/2017 | Hartmann et al. |
| 2017/0158613 A1 | 6/2017 | Schomaker et al. |

FOREIGN PATENT DOCUMENTS

| | | |
|---|---|---|
| DE | 198 19 187 | 11/1999 |
| EP | 0 851 023 A2 | 7/1998 |
| EP | 2 774 913 A1 | 9/2014 |
| JP | 56-47161 B2 | 11/1961 |
| JP | 61-153132 A | 7/1986 |
| JP | 11-137988 A | 5/1999 |
| JP | 2015-515531 A | 5/2015 |
| WO | WO 2009/103822 A1 | 8/2009 |
| WO | WO 2012/168739 A1 | 12/2012 |

(Continued)

OTHER PUBLICATIONS

International Search Report dated Sep. 29, 2017 in PCT/EP2017/063285 filed Jun. 1, 2017.

(Continued)

*Primary Examiner* — Gregory R Delcotto
(74) *Attorney, Agent, or Firm* — Arent Fox LLP

(57) ABSTRACT

Process for making a powder or granule containing at least one chelating agent selected from alkali metal salts of methyl glycine diacetic acid (MGDA) and glutamic acid diacetate (GLDA) and iminodisuccinic acid (IDS), said process comprising the steps of (a) introducing an aqueous solution or aqueous slurry of the respective chelating agent (A) into a spray-dryer or spray-granulator, and removing most of said water by spray-drying or spray granulation using a gas with an inlet temperature of 125 to 250° C., (b) withdrawingpowder or granules, respectively, from the spray-dryer or spray-granulator, respectively, (c) separating off fines from said powder or granules, wherein said fines have a maximum particle diameter of 350 μm, (d) separating off lumps from said powder or granules, wherein said lumps have a particle diameter of 1,500 μm or more, (e) milling said lumps to a maximum particle diameter of 500 μm, (f) re-introducing said fines from step (c) and milled lumps from step (e) into the spray-dryer or spray-granulator, wherein the share of fines is in the range of from 0.5 to 20% by weight of the total chelating agent (A) withdrawn in step (b) and the share of milled lumps is in the range of from 5 to 60% by weight of the total chelating agent (A) withdrawn in step (b).

8 Claims, No Drawings

(56) References Cited

FOREIGN PATENT DOCUMENTS

| WO | WO 2014/090943 A1 | 6/2014 |
| WO | WO 2015/121170 A1 | 8/2015 |
| WO | WO 2015/173157 A2 | 11/2015 |

OTHER PUBLICATIONS

Extended European Search Report dated Mar. 24, 2017 in corresponding European Patent Application No. 16175240.7, 5 pages.

POWDERS AND GRANULES AND PROCESS FOR MAKING SUCH POWDERS AND GRANULES

The present invention is directed towards a process for making a powder or granule containing
at least one chelating agent selected from alkali metal salts of methyl glycine diacetic acid ("MGDA") and glutamic acid diacetate ("GLDA") and iminodisuccinic acid ("IDS"),
said process comprising the steps of
(a) introducing an aqueous solution or aqueous slurry of the respective chelating agent (A) into a spray-dryer or spray-granulator, and removing most of said water by spray-drying or spray granulation using a gas with an inlet temperature of 125 to 250° C.,
(b) withdrawing powder or granules, respectively, from the spray-dryer or spray-granulator, respectively,
(c) separating off fines from said powder or granules, wherein said fines have a maximum particle diameter of 30 μm in the case of powders and a maximum particle diameter of 350 μm in the case of granules, respectively,
(d) separating off lumps from said powder or granules, wherein said lumps have a particle diameter of 250 μm or more in the case of powders and 1,500 μm or more in the case of granules, respectively,
(e) milling said lumps to a maximum particle diameter of 500 μm in the case of granules or to 40 μm in the case of powders, respectively,
(f) re-introducing said fines from step (c) and milled lumps from step (e) into the spray-dryer or spray-granulator,
wherein the share of fines is in the range of from 0.5 to 20% by weight of the total chelating agent (A) withdrawn in step (b) and the share of milled lumps from step (e) is in the range of from 5 to 60% by weight of the total chelating agent (A) withdrawn in step (b).

Furthermore, the present invention is directed towards certain powders and granules containing chelating agents.

Chelating agents of the aminocarboxylate type such as methyl glycine diacetic acid (MGDA) and glutamic acid diacetic acid (GLDA) and their respective alkali metal salts are useful sequestrants for alkaline earth metal ions such as $Ca^{2+}$ and $Mg^{2+}$. A lot of aminocarboxylates show good biodegradability and are thus environmentally friendly. For that reason, they are recommended and used for various purposes such as laundry detergents and for automatic dishwashing (ADW) formulations, in particular for so-called phosphate-free laundry detergents and phosphate-free ADW formulations.

Depending on the type of product—liquid home care and fabric care products versus solid home care and fabric care products—and the manufacturing process of solid home care and fabric care products care product manufacturers may either prefer to handle solutions of aminocarboxylates or solid arminocarboxylates, for example joint spray drying or solid mixing.

Powders and granules of aminocarboxylates may be shipped economically due to their high active ingredient content that goes along with low water content. Therefore, convenient processes for providing granules are still of great commercial interest.

In WO 2009/103822, a process is disclosed in which slurries are granulated that have a certain solids content, with a gas inlet temperature of 120° C. or less.

In WO 2012/168739, a process is disclosed wherein slurries of complexing agents are spray-dried under non-agglomerating conditions.

Both processes have their shortcomings. A low gas inlet temperature requires highly concentrated slurries or a huge amount of gas per unit of granule. A process using non-agglomerating conditions provides for powders only.

In many processes known from the prior art it has been suggested to remove the so-called fines, that are particles that are much smaller than the specified powder or granule, respectively, and to remove lumps, sometimes also referred to as "overs", and mill them to the desired size. Many processes known from the art, though, try to avoid the formation of major amounts of fines and lumps. The fines—and lumps—may be recycled but the formation of major amount obviously reduces the capacity of the drying vessel.

It is desired to provide chelating agents in solid form that are less hygroscopic and give no or little raise to yellowing upon contact with percarbonate. It is therefore an objective of the present invention to provide chelating agents in solid form that are less hygroscopic and give no or little raise to yellowing upon contact with percarbonate, and it is an objective of the present invention to provide a process for manufacturing such chelating agents in solid form.

Accordingly, the process defined at the outset has been found, hereinafter also referred to as inventive process or as process according to the present invention. The inventive process comprises several steps that may be referred to as step (a), step (b) etc. and that will be explained in more detail below.

It has been found a comparatively high amount of recycling of milled lumps and of fines that are to be recycled improve the product quality.

The inventive process is a process for making a powder or granule. In the context of the present invention, the term "powder" refers to particulate materials that are solids at ambient temperature and that preferably have an average particle diameter in the range of from 30 μm to less than 0.1 mm, preferably 30 μm up to 75 μm. The average particle diameter of inventive powders can be determined, e.g., by LASER diffraction methods, for example with Malvern apparatus, and refers to the volume average.

The term "granule" in the context of the present invention refers to particulate materials that are solids at ambient temperature and that preferably have an average particle diameter (D50) in the range of from 0.1 mm to 2 mm, preferably 0.4 mm to 1.25 mm, even more preferably 400 μm to 1 mm. The average particle diameter of inventive granules can be determined, e.g., by optical or preferably by sieving methods. Sieves employed may have a mesh in the range of from 60 to 3,000 μm.

In one embodiment of the present invention, inventive powders or inventive granules have a broad particle diameter distribution. In another embodiment of the present invention, inventive powders or inventive granules have a narrow particle diameter distribution. The particle diameter distribution can be adjusted, if desired, by multiple sieving steps.

Granules and powders made by the inventive process may contain residual moisture, moisture referring to water including water of crystallization and adsorbed water. The amount of water may be in the range of from 0.1 to 20% by weight, preferably 1 to 15% by weight, referring to the total solids content of the respective powder or granule, and may be determined by Karl-Fischer-titration or by drying at 160° C. to constant weight with infrared light.

Particles of powders and granules made by the inventive process may have regular or irregular shape. Preferred shapes of particles of powders and of granules made by the inventive process are spheroidal shapes.

Particles of powders or granules made by the inventive process contain at least one chelating agent, hereinafter also referred to as chelating agent (A). Chelating agent (A) is selected from alkali metal salts of methyl glycine diacetic acid (MGDA) and glutamic acid diacetate (GLDA) and iminodisuccinic acid (IDS).

Alkali metals of MGDA are selected from compounds according to general formula (I a)

$[CH_3-CH(COO)-N(CH_2-COO)_2]M_{3-x}H_x$ (I a)

wherein

M is selected from alkali metal cations, same or different, for example cations of lithium, sodium, potassium, rubidium, cesium, and combinations of at least two of the foregoing. Preferred examples of alkali metal cations are sodium and potassium and combinations of sodium and potassium.

x in formula (I a) is in the range of from zero to 1.0, preferred are zero to 0.5 or 0.1 to 0.4. In a particularly preferred embodiment, x is zero.

Alkali metals of GLDA are selected from compounds according to general formula (I b)

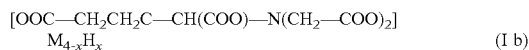

$[OOC-CH_2CH_2C-CH(COO)-N(CH_2-COO)_2]M_{4-x}H_x$ (I b)

wherein

M is selected from alkali metal cations, same or different, as defined above, x in formula (I b) is in the range of from zero to 2.0, preferred are zero to 0.5. In a particularly preferred embodiment, x is zero.

Alkali metals of IDS are selected from compounds according to general formula (I c)

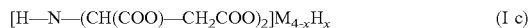

$[H-N-(CH(COO)-CH_2COO)_2]M_{4-x}H_x$ (I c)

wherein

M is selected from alkali metal cations, same or different, as defined above, x in formula (I c) is in the range of from zero to 2.0, preferred are zero to 0.5. In a particularly preferred embodiment, x is zero.

In one embodiment of the present invention, alkali metal salts of MGDA are selected from lithium salts, potassium salts and preferably sodium salts of MGDA. MGDA can be partially or preferably fully neutralized with the respective alkali. In a preferred embodiment, an average of from 2.7 to three COOH groups of MGDA is neutralized with alkali metal, preferably with sodium. In a particularly preferred embodiment, chelating agent (A) is the trisodium salt of MGDA.

MGDA and its respective alkali metal salts are selected from the racemic mixtures, the D-isomers and the L-isomers, and from mixtures of the D- and L-isomers other than the racemic mixtures. Preferably, MGDA and its respective alkali metal salts are selected from the racemic mixture and from mixtures containing in the range of from 55 to 85 mole-% of the L-isomer, the balance being D-isomer. Particularly preferred are mixtures containing in the range of from 60 to 80 mole-% of the L-isomer, the balance being D-isomer. Other particularly preferred embodiments are racemic mixtures.

GLDA and its respective alkali metal salts are selected from the racemic mixtures, the D-isomers and the L-isomers, and from mixtures of the D- and L-isomers other than the racemic mixtures. Preferably, GLDA and its respective alkali metal salts are selected from the racemic mixture and from mixtures containing in the range of from 55 to 99 mole-% of the L-isomer, the balance being D-isomer. Particularly preferred are mixtures containing in the range of from 60 to 98.5 mole-% of the L-isomer, the balance being D-isomer. Other particularly preferred embodiments are racemic mixtures.

IDS and its respective alkali metal salts are selected from various mixtures of isomers, for example D,D-IDS, L,L-IDS and D,L-IDS and combinations therefrom. Preferred are optically inactive mixtures since they are cheaper to be manufactured.

In any way, minor amounts of chelating agent (A) may bear a cation other than alkali metal. It is thus possible that minor amounts, such as 0.01 to 5 mol-% of total MGDA, GLDA or IDS, respectively, bear alkali earth metal cations such as $Mg^{2+}$ or $Ca^{2+}$, or an $Fe^{2+}$ cation.

In one embodiment of the present invention, alkali metal salt of chelating agent (A) may contain one or more impurities that may result from the synthesis of the respective chelating agent (A). In the cases of MGDA and GLDA and their alkali metal salts, such impurities may be selected from propionic acid, lactic acid, alanine, nitrilotriacetic acid (NTA) or the like and their respective alkali metal salts. In the case of IDS, such impurities may be selected from maleic acid, mono-amides of maleic/fumaric acid, and racemic asparagine. Such impurities are usually present in minor amounts. "Minor amounts" in this context refer to a total of 0.1 to 5% by weight, referring to alkali metal salt of chelating agent (A), preferably up to 2.5% by weight. In the context of the present invention, such minor amounts are neglected when determining the composition of granule made according to the inventive process.

In a special embodiment of the present invention, a combination alkali metal salts of at least two different chelating agents is used.

In step (a), an aqueous solution or aqueous slurry of the respective chelating agent (A) into a spray-dryer or spray-granulator.

Aqueous solutions are defined as solutions with no solid particles detectable by visual inspection. Aqueous slurries, as a contrast, contain solid particles. An aqueous slurry comprises a continuous phase and solids slurried in said continuous phase. The continuous phase of the slurry in step (a) comprises water and aminocarboxylic acid (A), and it is a saturated solution of aminocarboxylic acid. The continuous phase may also comprise one or more inorganic salts dissolved in the continuous phase, for example alkali metal hydroxide, alkali metal carbonate, alkali metal sulfate or alkali metal halide or a combination of at least two of the foregoing.

In one embodiment of the present invention, such aqueous solution may have a solids content in the range of from 10 to 55% by weight. Aqueous slurries according to step (a) may have a solids content in the range of from 42 to 80% by weight. In the case of slurries, the solids content refers to the sum of dissolved chelating agent (A) and precipitate.

In one embodiment of the present invention, such aqueous slurry or aqueous solution according to step (a) has a pH value in the range of from 8 to 14, preferably from 9 to 13.5 and even more preferably at least 9.5. The pH value is determined at ambient temperature and refers to the continuous phase.

The aqueous slurry or aqueous solution according to step (a) may have a temperature in the range of from 15 to 95° C., preferably 20 to 90° C. and even more preferably 50 to 90° C.

In step (a), said aqueous slurry or aqueous solution is introduced into a spray tower or spray granulator. A spray granulator usually contains a fluidized bed, in the context of the present invention it is a fluidized bed of chelating agent (A). In one embodiment of the present invention, the fluidized bed may have a temperature in the range of from 80 to 150° C., preferably 85 to 110° C.

Spraying is being performed through one or more nozzles per spray tower or spray granulator. Suitable nozzles are, for example, high-pressure rotary drum atomizers, rotary atomizers, three-fluid nozzles, single-fluid nozzles and two-fluid nozzles, single-fluid nozzles and two-fluid nozzles being preferred. The first fluid is the aqueous slurry or aqueous solution, respectively, the second fluid is compressed hot gas, also referred to as hot gas inlet stream, for example with a pressure of 1.1 to 7 bar. The hot gas inlet stream may have a temperature in the range of from at least 125° C. to 250° C., preferably 150 to 250° C., even more preferably 160 to 220° C.

In step (a), the aqueous slurry or aqueous solution of complexing agent (A) is introduced in the form of droplets. In one embodiment of the present invention, the droplets formed during the spray-granulating or spray-drying have an average diameter in the range of from 10 to 500 μm, preferably from 20 to 180 μm, even more preferably from 30 to 100 μm.

In one embodiment of the present invention, the off-gas departing the spray tower or spray granulator, respectively, may have a temperature in the range of from 40 to 140° C., preferably 80 to 110° C. but in any way colder than the hot gas stream. Preferably, the temperature of the off-gas departing the drying vessel and the temperature of the solid product present in the drying vessel are identical.

In one embodiment of the present invention, the pressure in the spray tower or spray granulator in step (a) is normal pressure ±100 mbar, preferably normal pressure ±20 mbar, for example one mbar less than normal pressure.

In one embodiment of the present invention, especially in a process for making an inventive granule, the average residence time of chelating agent (A) in step (a) is in the range of from 2 minutes to 4 hours, preferably from 30 minutes to 2 hours.

In another embodiment of the present invention, spray-granulation is being performed by performing two or more consecutive spray-drying processes, for example in a cascade of at least two spray dryers, for example in a cascade of at least two consecutive spray towers or a combination of a spray tower and a spray chamber, said spray chamber containing a fluidized bed. In the first dryer, a spray-drying process is being performed in the way as follows.

Spray-drying may be preferred in a spray dryer, for example a spray chamber or a spray tower. An aqueous slurry or solution with a temperature preferably higher than ambient temperature, for example in the range of from 50 to 95° C. is introduced into the spray dryer through one or more spray nozzles into a hot gas inlet stream, for example nitrogen or air, the solution or slurry being converted into droplets and the water being vaporized. The hot gas inlet stream may have a temperature in the range of from 125 to 350° C. The second spray dryer is charged with a fluidized bed with solid from the first spray dryer and solution or slurry obtained according to the above step is sprayed onto or into the fluidized bed, together with a hot gas inlet stream.

The hot gas inlet stream may have a temperature in the range of from 125 to 350° C., preferably 160 to 220° C.

In embodiments wherein an aged slurry is used, such aging may take in the range of from 2 hours to 24 hours at the temperature preferably higher than ambient temperature.

In the course of step (a), most of the water is removed. Most of the water shall mean that a residual moisture content of 0.1 to 20% by weight, referring to the powder or granule, remains.in embodiments that start of from a solution, about 51 to 75% by weight of the water present in the aqueous solution is removed in step (a).

In step (b), powder or granule, respectively, is removed from the spray tower or spray granulator. Said powder or granule has been at least partially formed in the course of step (a) of the inventive process. Said removal may be performed through one or more openings in the spray tower or spray granulator. Preferably, such one or more openings are at the bottom of the respective spray tower or spray granulator. Powder or granules, respectively, are removed including fines and lumps.

In embodiments in which a powder is made preferably 70 to 95% by weight of the solid formed are withdrawn from the spray tower per hour. In embodiments in which a granule is made, 20 to 60% of the fluidized bed are withdrawn per hour, for example with an extruder screw. Additional solids, especially fines, may be collected in the off-gas purification.

In step (c) of the inventive process, fines are separated off from said powder or granules, wherein said fines have a maximum particle diameter of 350 μm. Preferably, fines in processes wherein granules are desired may have a particles diameter in the range of from 1 to 150 μm. The act of separating off the fines may be performed by sieving or by air classification, preferably by sieving.

In embodiments wherein spray-drying is performed, fines have a particles diameter of 30 μm or less, for example 1 to 30 μm.

In one embodiment of the present invention, in step (c) 40 to 100% of the fines present in the respective material withdrawn in step (b) are separated off. In a preferred embodiment, in step (c) 80 to 99% by weight of the fines are separated off, and the residual 1 to 20% are left in the respective powder or granule. It is tedious to try to remove the fines quantitatively.

In step (d) of the inventive process, so-called lumps or "overs" are separated off from said powder or granules.

In embodiments wherein granules are desired, said lumps to be separated off are particles that have a minimum particle diameter of 1,000 μm, for example, 1,500 μm to 2 mm or even more. In a preferred embodiment, lumps are particles that have a minimum particle diameter of 1,250 μm or more, even more preferably 900 μm to 2 mm.

In embodiments wherein powders are desired, said lumps or overs have a minimum particle diameter of 250 μm or more, for example 250 to 1,000 μm.

Overs or lumps may be removed, e.g., with the help of a discharge screw or a rotary valve, usually together with desired product, and then classified.

It is observed that in connection with step (e), the smaller the maximum size of the lumps to be separated off in step (d) the better the hygroscopicity behavior of the later chelating agent, and the better the peroxide stability.

Steps (c) and (d) may be performed in any order, consecutively or simultaneously.

In one embodiment of the present invention, the amount of powder or granule, respectively, other than fines and overs is in the range of from 55 to 70% by weight, referring to total amount of material removed in step (b).

In step (e) of the inventive process, the lumps separated of in step (d) are milled down to a maximum particle diameter of 500 μm, preferably to a maximum particle diameter of 400 μm. The milling may be performed in any type of mills. Examples of particularly useful mills are jet mills, pin mills and bolting machines (German: Stiftmühlen). Further examples are roller mills and ball mills.

From step (e), a particulate material is obtained. It usually has a broad particle diameter distribution, in embodiments wherein granules are desired such particulate material may have particles that have a particle diameter in the range of from 1 to 500 μm.

In step (f) of the inventive process, said fines from step (c) and milled lumps from step (e) are reintroduced into the spray-dryer or spray-granulator. Such reintroducing may be performed by pneumatically transporting said fines from step (c) and milled lumps from step (e) into the spray tower or spray granulator, respectively, preferably through an extra opening rather than together with solution or slurry from step (a).

The share of fines withdrawn in step (b) is in the range of from 0.5 to 20% by weight of the total chelating agent (A) withdrawn in step (b), preferably 4 to 18% by weight. The share of lumps is in the range of from 5 to 60% by weight of the total chelating agent (A) withdrawn in step (b), preferably 20 to 40% by weight and even more preferably 25 to 35% by weight. With a higher share of lumps, the inventive process becomes economically unfavorable because it is too much recycling. With a lower share of lumps the hygroscopicity becomes too high.

In one embodiment of the present invention, chelating agent (A) is spray dried or spray granulated, respectively, without any additive such as a (co)polymer or silica or a surfactant. In other embodiments, chelating agent (A) is spray dried or spray granulated, respectively, with an additive selected from a (co)polymer, hereinafter referred to as (co)polymer (B), or with a polyvinyl alcohol or silica additive.

In one embodiment of the present invention, the aqueous solution or aqueous slurry from step (a) contains at least one additive selected from silica, silicates, inorganic salts, (co)polymers (B) and complexing agents other than aminocarboxylic acid (A) and organic (co)polymers. Such additive(s) may also be referred to as additive(s) (B). This may be accomplished by adding one or more additives (B) to the aqueous slurry or solution at any stage before step (b). Examples of useful additives (B) are, for example, titanium dioxide, sodium carbonate, potassium carbonate, sugar, silica gel, sodium silicate, potassium silicate, and (co)polymers (B) such as, but not limited to polyacrylates, polyalkylenimines such as polyethylenimines, alkoxylated polyethylenimines, carboxymethylated polyethylenimines, and polyvinyl alcohol. Polyvinyl alcohol in the context of the present invention refers to completely or partially hydrolyzed polyvinyl acetate. In partially hydrolyzed polyvinyl acetate, at least 95 mol-%, preferably at least 96 mol-% of the acetate groups have been hydrolyzed. Examples of complexing agents other than aminocarboxylic acid (A) are alkali metal citrates. Another possible class of additives is phosphonates, for example the alkali metal salts of 1-hydroxyethane 1,1-diphosphonic acid, "HEDP".

In one embodiment of the present invention polyvinyl alcohol has an average molecular weight $M_w$ in the range of from 22,500 to 115,000 g/mol, for example up to 40,000 g/mol. In one embodiment of the present invention polyvinyl alcohol has an average molecular weight $M_n$ in the range of from 2,000 to 40,000 g/mol.

In one embodiment of the present invention, the aqueous slurry subjected to spray-granulation in step (c) contains 0.05 to 30% by weight of additive(s) (B) in total, the percentage referring to the entire aqueous slurry. The amount of polyethylenimines or alkoxylated polyethylenimines is preferably in the range of from 0.05 to 0.5% by weight, the amount of silicate may be up to 30% by weight.

Examples of (co)polymers (B) are poly(meth)acrylates, polyalkylenimines, especially polyethylenimines, and substituted polyalkylenimines, for examples polycarboxymethylated polyethylenimines, polycarboxyethylated polyethylenimines, and polyaylkoxylated polyethylenimines, especially polyethoxylated polyethylenimines.

Preferred examples of polycarbomethoxylated polyethylenimines are polyethylenimines in which 20 to 90 mole-% of the N-atoms bear at least one $CH_2COO^-$ group, and their respective alkali metal salts, especially their sodium salts.

In one embodiment of the present invention said slurry or solution in to step (a) contains in the range of from 80 to 99.9% by weight chelating agent (A) and 0.1 to 20% by weight (co)polymer (B), percentages referring to the total solids content of said aqueous slurry or solution.

In one embodiment of the present invention, (co)polymers (B) selected from poly(meth)acrylic acid have an average molecular weight $M_w$ in the range of from 1,200 to 30,000 g/mol, determined by gel permeation chromatography and referring to the respective free acid, if applicable.

In one embodiment of the present invention the aqueous solution or slurry in step (a) contains at least one (co)polymer (B), said (co)polymer (B) being selected from homo- and copolymers of (meth)acrylic acid and polyalkylenimines that may be polyalkoyxylated or substituted with carboxymethyl groups.

In one embodiment of the present invention, the inventive process may comprise one or more additional steps (g). For example, a post-drying step (g) is possible, sometimes also referred to as thermal after-treatment, preferably after step (b) on the material that is neither fines nor lumps. Thermal after-treatment may be performed in a drying oven, for example at a temperature in the range from 80 to 120° C., or with hot steam, preferably at 100 to 160° C.

By performing the inventive process, powders and granules with excellent properties may be manufactured. They do not only exhibit good properties with respect to biodegradability and complexing behavior but also show low hygroscopicity and an excellent behavior towards peroxides and percarbonates.

Another aspect of the present invention are powders and granules containing at least one chelating agent selected from methyl glycine diacetic acid (MGDA) and glutamic acid diacetate (GLDA) and iminodisuccinic acid (IDS) and their respective alkali metal salts, said powders and granules hereinafter also being referred to as inventive powders and as inventive granules, respectively.

Inventive powders and inventive granules contain
(A) at least one chelating agent selected from methyl glycine diacetic acid (MGDA) and glutamic acid diacetate (GLDA) and iminodisuccinic acid (IDS) and their respective alkali metal salts, with a degree of crystallinity in the range of from 75 to 86%, determined by X-ray diffraction.

Chelating agents (A) have been explained in detail above.

The degree of crystallinity, in the context of the present invention also simply referred to as crystallinity, was determined from the X-ray powder diffractograms in a known manner by, as usual, determining the surface fraction of the crystalline phase and of the amorphous phase and using these to calculate the degree of crystallinity, CD, as ratio of the area of the crystalline phase, $I_c$, to the total area, consisting of the combined areas of the amorphous phase, $I_a$, and the area of the crystalline phase, $I_c$:

$$CD=I_c/(I_c+I_a).$$

In particular, the determination of the degree of crystallinity can be carried out by using a software program, for example the software program TOPAS® from Bruker AXS.

The determination of the degree of crystallinity was performed using X-ray powder diffraction, according to the method of relative intensities. Data is collected on a standard Bragg-Brentano diffractometer, using CuKα radiation. The region of 2° to 50° (2θ) is scanned using a step size of 0.02°. A primary and secondary programmable motorized slit are set to ensure a constant illuminated sample length of 20 mm. The diffraction pattern is modelled using the Rietveld approach matching the calculated diffraction pattern to the experimental data. The following parameters enter into the model: linear background function, Lorentz- and polarization correction, the entire crystal structures of Form I and Form II of MGDA-Na$_3$. The latter contribute the crystalline intensity ($I_{crystalline}$) toward the modelled pattern. The amorphous intensity ($I_{amorphous}$) is modelled using two Lorentzian functions with centres at 8° (2θ) and 36.2° 2θ). The positions, intensities and peak widths were refined to match the measured data. This model was set up and refined in the commercial software TOPAS V4.2 (Bruker AXS GmbH, Karlsruhe). The crystallinity Kwas then determined using the function:

$$K = \frac{I_{crystalline}}{I_{crystalline} + I_{amorphous}}$$

In accordance with the explanations above, inventive powders and inventive granules may exist as racemic mixture (D,L) or as pure L- or D-enantiomer—of which the L-enantiomer is preferred—or as mixture of L- and D-enantiomers in which one of the enantiomers is predominantly present, for example in mixtures with an enantiomeric excess (ee) of the L-enantiomer in the range of from 0.1 to 85%. Preferred are racemic mixtures and mixtures of enantiomers containing pre-dominantly the respective L-isomer with an enantiomeric excess (ee) in the range of from 0.1 to 85%, even more preferred from 2.5% to 50%.

In one embodiment of the present invention, inventive powders and inventive granules have a residual moisture content in the range of from 1 to 20% by weight. The residual moisture content may be determined by Karl-Fischer titration or by drying at 160° C. to constant weight with infrared light.

In one embodiment of the present invention, inventive powders have an average diameter in the range of from 30 µm to 95 µm, especially from 30 to 75 µm.

In one embodiment of the present invention, inventive granule has an average particle diameter in the range of from 0.35 mm to 1.5 mm, preferably from 350 to 1,000 µm, even more preferably up to 900 µm. The highest number of particles preferably has an average particle diameter in the range of from 600 to 750 µm.

Another aspect of the present invention relates to the use of inventive powders and inventive granules, and another aspect of the present invention relates to methods of use of the inventive powders and inventive granules. The preferred use of inventive powders and inventive granules is for the manufacture of solid laundry detergent compositions and of solid detergent compositions for hard surface cleaning. Solid laundry detergent compositions and solid detergent compositions for hard surface cleaning may contain some residual moisture, for example 0.1 to 10% by weight, but are otherwise solid mixtures. The residual moisture content may be determined, e.g., under vacuum at 80° C. Another aspect of the present invention relates to solid laundry detergent compositions and to solid detergent compositions for hard surface cleaning.

In the context of the present invention, the term "detergent composition for cleaners" includes cleaners for home care and for industrial or institutional applications. The term "detergent composition for hard surface cleaners" includes compositions for dishwashing, especially hand dishwash and automatic dishwashing and ware-washing, and compositions for other hard surface cleaning such as, but not limited to compositions for bathroom cleaning, kitchen cleaning, floor cleaning, descaling of pipes, window cleaning, car cleaning including truck cleaning, furthermore, open plant cleaning, cleaning-in-place, metal cleaning, disinfectant cleaning, farm cleaning, high pressure cleaning, but not laundry detergent compositions.

In the context of the present invention and unless expressly stated otherwise, percentages in the context of ingredients of laundry detergent compositions are percentages by weight and refer to the total solids content of the respective laundry detergent composition. In the context of the present invention and unless expressly stated otherwise, percentages in the context of ingredients of detergent composition for hard surface cleaning are percentages by weight and refer to the total solids content of the detergent composition for hard surface cleaner.

In one embodiment of the present invention, solid laundry detergent compositions according to the present invention may contain in the range of from 1 to 30% by weight of inventive powder or inventive granule, respectively. Percentages refer to the total solids content of the respective laundry detergent composition.

In one embodiment of the present invention, inventive solid detergent compositions for hard surface cleaning may contain in the range of from 1 to 50% by weight of inventive powder or inventive granule, respectively, preferably 5 to 40% by weight and even more preferably 10 to 25% by weight. Percentages refer to the total solids content of the respective detergent composition for hard surface cleaning.

Particularly advantageous inventive solid detergent compositions for hard surface cleaning and inventive solid laundry detergent compositions, especially for home care, may contain one or more complexing agent other than inventive powder and inventive granule. Inventive solid detergent compositions for hard surface cleaning and inventive solid laundry detergent compositions may contain one or more complexing agent (in the context of the present invention also referred to as sequestrant) other than an inventive powder or inventive granule. Examples are citrate, phosphonic acid derivatives, for example the disodium salt of hydroxyethane-1,1-diphosphonic acid ("HEDP"), and polymers with complexing groups like, for example, polyethyleneimine in which 20 to 90 mole-% of the N-atoms bear at least one $CH_2COO^-$ group, and their respective alkali metal salts, especially their sodium salts, for example GLDA-Na$_4$, IDS-Na$_4$, and trisodium citrate, and phosphates such as STPP (sodium tripolyphosphate). Due to the fact that phosphates raise environmental concerns, it is preferred that advantageous detergent compositions for cleaners and advantageous laundry detergent compositions are free from phosphate. "Free from phosphate" should be understood in the context of the present invention, as meaning that the content of phosphate and polyphosphate is in sum in the range from 10 ppm to 0.2% by weight, determined by gravimetry.

Preferred inventive solid detergent compositions for hard surface cleaning and preferred inventive solid laundry detergent compositions may contain one or more surfactant, preferably one or more non-ionic surfactant.

Preferred non-ionic surfactants are alkoxylated alcohols, di- and multiblock copolymers of ethylene oxide and propylene oxide and reaction products of sorbitan with ethylene oxide or propylene oxide, alkyl polyglycosides (APG), hydroxyalkyl mixed ethers and amine oxides.

Preferred examples of alkoxylated alcohols and alkoxylated fatty alcohols are, for example, compounds of the general formula (III)

$$R^3-O-[\phantom{x}\phantom{x}-O-]_e[\phantom{x}\phantom{x}-O-]_f R^4 \quad (III)$$
$$\phantom{xxxxxxxxxxxxxxxxxxxxx} R^2$$

in which the variables are defined as follows:
  $R^2$ is identical or different and selected from hydrogen and linear $C_1$-$C_{10}$-alkyl, preferably in each case identical and ethyl and particularly preferably hydrogen or methyl,
  $R^3$ is selected from $C_8$-$C_{22}$-alkyl, branched or linear, for example n-$C_8H_{17}$, n-$C_{10}H_{21}$, n-$C_{12}H_{25}$, n-$C_{14}H_{29}$, n-$C_{16}H_{33}$ or n-$C_{18}H_{37}$,
  $R^4$ is selected from $C_1$-$C_{10}$-alkyl, methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl or isodecyl,
  e and f are in the range from zero to 300, where the sum of e and f is at least one, preferably in the range of from 3 to 50. Preferably, e is in the range from 1 to 100 and f is in the range from 0 to 30.

In one embodiment, compounds of the general formula (III) may be block copolymers or random copolymers, preference being given to block copolymers.

Other preferred examples of alkoxylated alcohols are, for example, compounds of the general formula (IV)

$$R^5-O-[\phantom{x}\phantom{x}-O-]_a[\phantom{x}\phantom{x}-O-]_b[\phantom{x}\phantom{x}-O-]_d H \quad (IV)$$
$$\phantom{xx}R^2 \phantom{xxxxx} R^2$$

in which the variables are defined as follows:
  $R^2$ is identical or different and selected from hydrogen and linear $C_1$-$C_0$-alkyl, preferably identical in each case and ethyl and particularly preferably hydrogen or methyl,
  $R^5$ is selected from $C_6$-$C_{20}$-alkyl, branched or linear, in particular n-$C_8H_{17}$, n-$C_{10}H_{21}$, n-$C_{12}H_{25}$, n-$C_{13}H_{27}$, n-$C_{15}H_{31}$, n-$C_{14}H_{29}$, n-$C_{16}H_{33}$, n-$C_{18}H_{37}$,
  a is a number in the range from zero to 10, preferably from 1 to 6,
  b is a number in the range from 1 to 80, preferably from 4 to 20,
  d is a number in the range from zero to 50, preferably 4 to 25.

The sum a+b+d is preferably in the range of from 5 to 100, even more preferably in the range of from 9 to 50.

Preferred examples for hydroxyalkyl mixed ethers are compounds of the general formula (V)

$$R^3-O-[\phantom{x}\phantom{x}-O-]_m[\phantom{x}\phantom{x}-O-]_n \overset{OH}{\underset{}{\phantom{x}}} R^5 \quad (V)$$
$$\phantom{xxxxxxxxxxxxxxxx} R^2$$

in which the variables are defined as follows:
  $R^2$ is identical or different and selected from hydrogen and linear $C_1$-$C_{10}$-alkyl, preferably in each case identical and ethyl and particularly preferably hydrogen or methyl,
  $R^3$ is selected from $C_8$-$C_{22}$-alkyl, branched or linear, for example iso-$C_{11}H_{23}$, iso-$C_{13}H_{27}$, n-$C_8H_{17}$, n-$C_{10}H_{21}$, n-$C_{12}H_{25}$, n-$C_{14}H_{29}$, n-$C_{16}H_{33}$ or n-$C_{18}H_{37}$,
  $R^5$ is selected from $C_6$-$C_{20}$-alkyl, for example n-hexyl, isohexyl, sec-hexyl, n-heptyl, n-octyl, 2-ethylhexyl, n-nonyl, n-decyl, isodecyl, n-dodecyl, n-tetradecyl, n-hexadecyl, and n-octadecyl.

The variables m and n are in the range from zero to 300, where the sum of n and m is at least one, preferably in the range of from 5 to 50. Preferably, m is in the range from 1 to 100 and n is in the range from 0 to 30.

Compounds of the general formula (IV) and (V) may be block copolymers or random copolymers, preference being given to block copolymers.

Further suitable nonionic surfactants are selected from di- and multiblock copolymers, composed of ethylene oxide and propylene oxide. Further suitable nonionic surfactants are selected from ethoxylated or propoxylated sorbitan esters. Amine oxides or alkyl polyglycosides, especially linear $C_4$-$C_{16}$-alkyl polyglucosides and branched $C_8$-$C_{14}$-alkyl polyglycosides such as compounds of general average formula (VI) are likewise suitable.

$$R^7 \phantom{xx} O-(G^1)_y \quad (VI)$$
$$\phantom{xxx}\diagdown\phantom{x}\diagup\phantom{xxx}$$
$$\phantom{xxxxxxxx}\diagdown H$$
$$R^6$$

wherein:
  $R^6$ is $C_1$-$C_4$-alkyl, in particular ethyl, n-propyl or isopropyl,
  $R^7$ is —$(CH_2)_2$—$R^6$,
  $G^1$ is selected from monosaccharides with 4 to 6 carbon atoms, especially from glucose and xylose,
  y in the range of from 1.1 to 4, y being an average number, Further examples of non-ionic surfactants are compounds of general formula (VII) and (VIII)

$$R^5-\overset{O}{\underset{}{C}}-O-(AO)_w-R^8 \quad (VII)$$

-continued

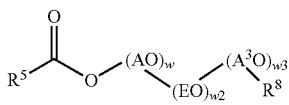
(VIII)

AO is selected from ethylene oxide, propylene oxide and butylene oxide,

EO is ethylene oxide, $CH_2CH_2$—O, $R^8$ selected from $C_8$-$C_{18}$-alkyl, branched or linear, and $R^5$ is defined as above.

$A^3O$ is selected from propylene oxide and butylene oxide, w is a number in the range of from 15 to 70, preferably 30 to 50, w1 and w3 are numbers in the range of from 1 to 5, and w2 is a number in the range of from 13 to 35.

An overview of suitable further nonionic surfactants can be found in EP-A 0 851 023 and in DE-A 198 19 187.

Mixtures of two or more different nonionic surfactants selected from the foregoing may also be present.

Other surfactants that may be present are selected from amphoteric (zwitterionic) surfactants and anionic surfactants and mixtures thereof.

Examples of amphoteric surfactants are those that bear a positive and a negative charge in the same molecule under use conditions. Preferred examples of amphoteric surfactants are so-called betaine-surfactants. Many examples of betaine-surfactants bear one quaternized nitrogen atom and one carboxylic acid group per molecule. A particularly preferred example of amphoteric surfactants is cocamidopropyl betaine (lauramidopropyl betaine).

Examples of amine oxide surfactants are compounds of the general formula (IX)

$$R^9R^{10}R^{11}N \to O \quad (IX)$$

wherein $R^9$, $R^{10}$, and $R^{11}$ are selected independently from each other from aliphatic, cycloaliphatic or $C_2$-$C_4$-alkylene $C_{10}$-$C_{20}$-alkylamido moieties. Preferably, $R^9$ is selected from $C_8$-$C_{20}$-alkyl or $C_2$-$C_4$-alkylene $C_{10}$-$C_{20}$-alkylamido and $R^{10}$ and $R^{11}$ are both methyl.

A particularly preferred example is lauryl dimethyl aminoxide, sometimes also called lauramine oxide. A further particularly preferred example is cocamidylpropyl dimethylaminoxide, sometimes also called cocamidopropylamine oxide.

Examples of suitable anionic surfactants are alkali metal and ammonium salts of $C_8$-$C_{18}$-alkyl sulfates, of $C_8$-$C_{18}$-fatty alcohol polyether sulfates, of sulfuric acid half-esters of ethoxylated $C_4$-$C_{12}$-alkylphenols (ethoxylation: 1 to 50 mol of ethylene oxide/mol), $C_{12}$-$C_{18}$ sulfo fatty acid alkyl esters, for example of $C_{12}$-$C_{18}$ sulfo fatty acid methyl esters, furthermore of $C_{12}$-$C_{18}$-alkylsulfonic acids and of $C_{10}$-$C_{18}$-alkylarylsulfonic acids. Preference is given to the alkali metal salts of the aforementioned compounds, particularly preferably the sodium salts.

Further examples for suitable anionic surfactants are soaps, for example the sodium or potassium salts of stearic acid, oleic acid, palmitic acid, ether carboxylates, and alkylether phosphates.

Preferably, inventive laundry detergent compositions contain at least one anionic surfactant.

In one embodiment of the present invention, inventive solid laundry detergent compositions may contain 0.1 to 60% by weight of at least one surfactant, selected from anionic surfactants, amphoteric surfactants and amine oxide surfactants.

In one embodiment of the present invention, inventive solid detergent compositions for cleaners may contain 0.1 to 60% by weight of at least one surfactant, selected from anionic surfactants, amphoteric surfactants and amine oxide surfactants.

In a preferred embodiment, inventive solid detergent compositions for cleaners and especially those for automatic dishwashing do not contain any anionic surfactant.

Inventive solid detergent compositions for hard surface cleaning and inventive solid laundry detergent compositions may contain at least one bleaching agent, also referred to as bleach. Bleaching agents may be selected from chlorine bleach and peroxide bleach, and peroxide bleach may be selected from inorganic peroxide bleach and organic peroxide bleach. Preferred are inorganic peroxide bleaches, selected from alkali metal percarbonate, alkali metal perborate and alkali metal persulfate.

Examples of organic peroxide bleaches are organic percarboxylic acids, especially organic percarboxylic acids.

In inventive solid detergent compositions for hard surface cleaning and in inventive solid laundry detergent compositions, alkali metal percarbonates, especially sodium percarbonates, are preferably used in coated form. Such coatings may be of organic or inorganic nature. Examples are glycerol, sodium sulfate, silicate, sodium carbonate, and combinations of at least two of the foregoing, for example combinations of sodium carbonate and sodium sulfate.

Suitable chlorine-containing bleaches are, for example, 1,3-dichloro-5,5-dimethylhydantoin, N-chlorosulfamide, chloramine T, chloramine B, sodium hypochlorite, calcium hypochlorite, magnesium hypochlorite, potassium hypochlorite, potassium dichloroisocyanurate and sodium dichloroisocyanurate.

Inventive solid detergent compositions for hard surface cleaning and inventive solid laundry detergent compositions may comprise, for example, in the range from 3 to 10% by weight of chlorine-containing bleach.

Inventive solid detergent compositions for hard surface cleaning and inventive solid laundry detergent compositions may comprise one or more bleach catalysts. Bleach catalysts can be selected from bleach-boosting transition metal salts or transition metal complexes such as, for example, manganese-, iron-, cobalt-, ruthenium- or molybdenum-salen complexes or carbonyl complexes. Manganese, iron, cobalt, ruthenium, molybdenum, titanium, vanadium and copper complexes with nitrogen-containing tripod ligands and also cobalt-, iron-, copper- and ruthenium-amine complexes can also be used as bleach catalysts.

Inventive solid detergent compositions for hard surface cleaning and inventive solid laundry detergent compositions may comprise one or more bleach activators, for example N-methylmorpholinium-acetonitrile salts ("MMA salts"), trimethylammonium acetonitrile salts, N-acylimides such as, for example, N-nonanoylsuccinimide, 1,5-diacetyl-2,2-dioxohexahydro-1,3,5-triazine ("DADHT") or nitrile quats (trimethylammonium acetonitrile salts).

Further examples of suitable bleach activators are tetraacetylethylenediamine (TAED) and tetraacetylhexylenediamine.

Inventive solid detergent compositions for hard surface cleaning and inventive solid laundry detergent compositions may comprise one or more corrosion inhibitors. In the present case, this is to be understood as including those compounds which inhibit the corrosion of metal. Examples of suitable corrosion inhibitors are triazoles, in particular benzotriazoles, bisbenzotriazoles, aminotriazoles, alkylaminotriazoles, also phenol derivatives such as, for example, hydroquinone, pyrocatechol, hydroxyhydroquinone, gallic acid, phloroglucinol or pyrogallol.

In one embodiment of the present invention, inventive solid detergent compositions for hard surface cleaning and inventive solid laundry detergent compositions comprise in total in the range from 0.1 to 1.5% by weight of corrosion inhibitor.

Inventive solid detergent compositions for hard surface cleaning and inventive solid laundry detergent compositions may comprise one or more builders, selected from organic and inorganic builders. Examples of suitable inorganic builders are sodium sulfate or sodium carbonate or silicates, in particular sodium disilicate and sodium metasilicate, zeolites, sheet silicates, in particular those of the formula $\alpha$-$Na_2Si_2O_5$, $\beta$-$Na_2Si_2O_5$, and $\delta$-$NA_2Si_2O_5$, also fatty acid sulfonates, $\alpha$-hydroxypropionic acid, alkali metal malonates, fatty acid sulfonates, alkyl and alkenyl disuccinates, tartaric acid diacetate, tartaric acid monoacetate, oxidized starch, and polymeric builders, for example polycarboxylates and polyaspartic acid.

Examples of organic builders are especially polymers and copolymers. In one embodiment of the present invention, organic builders are selected from polycarboxylates, for example alkali metal salts of (meth)acrylic acid homopolymers or (meth)acrylic acid copolymers.

Suitable comonomers are monoethylenically unsaturated dicarboxylic acids such as maleic acid, fumaric acid, maleic anhydride, itaconic acid and citraconic acid. A suitable polymer is in particular polyacrylic acid, which preferably has an average molecular weight $M_w$ in the range from 2000 to 40 000 g/mol, preferably 2000 to 10 000 g/mol, in particular 3000 to 8000 g/mol. Also of suitability are copolymeric polycarboxylates, in particular those of acrylic acid with methacrylic acid and of acrylic acid or methacrylic acid with maleic acid and/or fumaric acid, and in the same range of molecular weight.

It is also possible to use copolymers of at least one monomer from the group consisting of monoethylenically unsaturated $C_3$-$C_{10}$-mono- or $C_4$-$C_{10}$-dicarboxylic acids or anhydrides thereof, such as maleic acid, maleic anhydride, acrylic acid, methacrylic acid, fumaric acid, itaconic acid and citraconic acid, with at least one hydrophilic or hydrophobic monomer as listed below.

Suitable hydrophobic monomers are, for example, isobutene, diisobutene, butene, pentene, hexene and styrene, olefins with 10 or more carbon atoms or mixtures thereof, such as, for example, 1-decene, 1-dodecene, 1-tetradecene, 1-hexadecene, 1-octadecene, 1-eicosene, 1-docosene, 1-tetracosene and 1-hexacosene, $C_{22}$-$\alpha$-olefin, a mixture of $C_{20}$-$C_{24}$-$\alpha$-olefins and polyisobutene having on average 12 to 100 carbon atoms per molecule.

Suitable hydrophilic monomers are monomers with sulfonate or phosphonate groups, and also nonionic monomers with hydroxyl function or alkylene oxide groups. By way of example, mention may be made of: allyl alcohol, isoprenol, methoxypolyethylene glycol (meth)acrylate, methoxypolypropylene glycol (meth)acrylate, methoxypolybutylene glycol (meth)acrylate, methoxypoly(propylene oxide-co-ethylene oxide) (meth)acrylate, ethoxypolyethylene glycol (meth)acrylate, ethoxypolypropylene glycol (meth)acrylate, ethoxypolybutylene glycol (meth)acrylate and ethoxypoly(propylene oxide-co-ethylene oxide) (meth)acrylate. Polyalkylene glycols here may comprise 3 to 50, in particular 5 to 40 and especially 10 to 30 alkylene oxide units per molecule.

Particularly preferred sulfonic-acid-group-containing monomers here are 1-acrylamido-1-propanesulfonic acid, 2-acrylamido-2-propanesulfonic acid, 2-acrylamido-2-methylpropanesulfonic acid, 2-methacrylamido-2-methylpropanesulfonic acid, 3-methacrylamido-2-hydroxypropanesulfonic acid, allylsulfonic acid, methallylsulfonic acid, allyloxybenzenesulfonic acid, methallyloxybenzenesulfonic acid, 2-hydroxy-3-(2-propenyloxy)propanesulfonic acid, 2-methyl-2-propene-1-sulfonic acid, styrenesulfonic acid, vinylsulfonic acid, 3-sulfopropyl acrylate, 2-sulfoethyl methacrylate, 3-sulfopropyl methacrylate, sulfomethacrylamide, sulfomethylmethacrylamide, and salts of said acids, such as sodium, potassium or ammonium salts thereof.

Particularly preferred phosphonate-group-containing monomers are vinylphosphonic acid and its salts.

A further example of builders is carboxymethyl inulin.

Moreover, amphoteric polymers can also be used as builders.

Inventive solid detergent compositions for hard surface cleaning and inventive solid laundry detergent compositions may comprise, for example, in the range from in total 10 to 70% by weight, preferably up to 50% by weight, of builder. In the context of the present invention, MGDA is not counted as builder.

In one embodiment of the present invention, inventive solid detergent compositions for hard surface cleaning and inventive solid laundry detergent compositions may comprise one or more cobuilders.

Inventive solid detergent compositions for hard surface cleaning and inventive solid laundry detergent compositions may comprise one or more antifoams, selected for example from silicone oils and paraffin oils.

In one embodiment of the present invention, inventive solid detergent compositions for hard surface cleaning and inventive solid laundry detergent compositions comprise in total in the range from 0.05 to 0.5% by weight of antifoam.

Inventive solid detergent compositions for hard surface cleaning and inventive solid laundry detergent compositions may comprise one or more enzymes. Examples of enzymes are lipases, hydrolases, amylases, proteases, cellulases, esterases, pectinases, lactases and peroxidases.

In one embodiment of the present invention, inventive solid detergent compositions for hard surface cleaning and inventive solid laundry detergent compositions may comprise, for example, up to 5% by weight of enzyme, preference being given to 0.1 to 3% by weight. Said enzyme may be stabilized, for example with the sodium salt of at least one $C_1$-$C_3$-carboxylic acid or $C_4$-$C_{10}$-dicarboxylic acid. Preferred are formates, acetates, adipates, and succinates.

In one embodiment of the present invention, inventive solid detergent compositions for hard surface cleaning and inventive solid laundry detergent compositions comprise at least one zinc salt. Zinc salts can be selected from water-soluble and water-insoluble zinc salts. In this connection, within the context of the present invention, water-insoluble is used to refer to those zinc salts which, in distilled water at 25° C., have a solubility of 0.1 g/l or less. Zinc salts which have a higher solubility in water are accordingly referred to within the context of the present invention as water-soluble zinc salts.

In one embodiment of the present invention, zinc salt is selected from zinc benzoate, zinc gluconate, zinc lactate, zinc formate, $ZnCl_2$, $ZnSO_4$, zinc acetate, zinc citrate, $Zn(NO_3)_2$, $Zn(CH_3SO_3)_2$ and zinc gallate, preferably $ZnCl_2$, $ZnSO_4$, zinc acetate, zinc citrate, $Zn(NO_3)_2$, $Zn(CH_3SO_3)_2$ and zinc gallate.

In another embodiment of the present invention, zinc salt is selected from ZnO, ZnO.aq, $Zn(OH)_2$ and $ZnCO_3$. Preference is given to ZnO.aq.

In one embodiment of the present invention, zinc salt is selected from zinc oxides with an average particle diameter (weight-average) in the range from 10 nm to 100 µm.

The cation in zinc salt can be present in complexed form, for example complexed with ammonia ligands or water ligands, and in particular be present in hydrated form. To simplify the notation, within the context of the present invention, ligands are generally omitted if they are water ligands.

Depending on how the pH of mixture according to the invention is adjusted, zinc salt can change. Thus, it is for example possible to use zinc acetate or $ZnCl_2$ for preparing formulation according to the invention, but this converts at a pH of 8 or 9 in an aqueous environment to ZnO, $Zn(OH)_2$ or ZnO.aq, which can be present in non-complexed or in complexed form.

Zinc salt may be present in those detergent compositions for cleaners according to the invention which are solid at room temperature are preferably present in the form of particles which have for example an average diameter (number-average) in the range from 10 nm to 100 µm, preferably 100 nm to 5 µm, determined for example by X-ray scattering.

Zinc salt may be present in those detergent compositions for home which are liquid at room temperature in dissolved or in solid or in colloidal form.

In one embodiment of the present invention, detergent compositions for cleaners and laundry detergent compositions comprise in total in the range from 0.05 to 0.4% by weight of zinc salt, based in each case on the solids content of the composition in question.

Here, the fraction of zinc salt is given as zinc or zinc ions. From this, it is possible to calculate the counterion fraction.

In one embodiment of the present invention, inventive solid detergent compositions for hard surface cleaning and inventive solid laundry detergent compositions are free from heavy metals apart from zinc compounds. Within the context of the present, this may be understood as meaning that detergent compositions for cleaners and laundry detergent compositions according to the invention are free from those heavy metal compounds which do not act as bleach catalysts, in particular of compounds of iron and of bismuth. Within the context of the present invention, "free from" in connection with heavy metal compounds is to be understood as meaning that the content of heavy metal compounds which do not act as bleach catalysts is in sum in the range from 0 to 100 ppm, determined by the leach method and based on the solids content. Preferably, formulation according to the invention has, apart from zinc, a heavy metal content below 0.05 ppm, based on the solids content of the formulation in question. The fraction of zinc is thus not included.

Within the context of the present invention, "heavy metals" are defined to be any metal with a specific density of at least 6 $g/cm^3$ with the exception of zinc. In particular, the heavy metals are metals such as bismuth, iron, copper, lead, tin, nickel, cadmium and chromium.

Preferably, inventive solid detergent compositions for hard surface cleaning and inventive solid laundry detergent compositions comprise no measurable fractions of bismuth compounds, i.e. for example less than 1 ppm.

In one embodiment of the present invention, inventive solid detergent compositions for hard surface cleaning and inventive solid laundry detergent compositions comprise one or more further ingredient such as fragrances, dyestuffs, organic solvents, buffers, disintegrants for tabs, and/or acids such as methylsulfonic acid.

Preferred example detergent compositions for automatic dishwashing may be selected according to table 1.

TABLE 1

Example detergent compositions for automatic dishwashing

| All amounts in g/sample | ADW.1 | ADW.2 | ADW.3 |
|---|---|---|---|
| inventive granule, racemic MGDA-$Na_3$, (D50): 550 µm | 30 | 22.5 | 15 |
| Protease | 2.5 | 2.5 | 2.5 |
| Amylase | 1 | 1 | 1 |
| n-$C_{18}H_{37}$—$O(CH_2CH_2O)_9H$ | 5 | 5 | 5 |
| Polyacrylic acid $M_w$ 4000 g/mol as sodium salt, completely neutralized | 10 | 10 | 10 |
| Sodium percarbonate | 10.5 | 10.5 | 10.5 |
| TAED | 4 | 4 | 4 |
| $Na_2Si_2O_5$ | 2 | 2 | 2 |
| $Na_2CO_3$ | 19.5 | 19.5 | 19.5 |
| Sodium citrate dihydrate | 15 | 22.5 | 30 |
| HEDP | 0.5 | 0.5 | 0.5 |
| ethoxylated polyethylenimine, 20 EO/NH group, $M_n$: 30,000 g/mol | option-ally: 0.1 | option-ally: 0.1 | option-ally: 0.1 |

Laundry detergent compositions according to the invention are useful for laundering any type of laundry, and any type of fibres. Fibres can be of natural or synthetic origin, or they can be mixtures of natural of natural and synthetic fibres. Examples of fibers of natural origin are cotton and wool. Examples for fibers of synthetic origin are polyurethane fibers such as Spandex® or Lycra®, polyester fibers, or polyamide fibers. Fibers may be single fibers or parts of textiles such as knitwear, wovens, or nonwovens.

The invention is further illustrated by working examples.

General remarks:

The X-ray powder diffractometer measurements were carried out on a D8 Advance® diffractometer from Bruker AXS (Karlsruhe). In reflection with Cu-K α-radiation was measured with a variable diaphragm adjustment on the primary side and on the secondary side. The measurement range was 2° to 80° 2-theta, the step width 0.01° and the measurement time per angle step 3.6 seconds.

The hygroscopicity was determined by storing at 25° C. and 50% relative humidity over a period of 24 hours. In the alternative, so-called tropic conditions are storing at 35° C. and 70 to 90% relative humidity over a period of 24 hours. Grade: from zero (free flowable granule/powder) to 4 (granule/powder has dissolved)

With exception of ee values and of degrees of crystallinity, percentages in the context of the examples refer to percent by weight unless expressly indicated otherwise.

Normal pressure: 1013 mbar

Average particle diameters are (D50) values and are determined by sieving methods unless expressly noted otherwise.

Chelating agent (A.1): MGDA-$Na_3$ (65% L-MGDA-$Na_3$, 35% D-MGDA-$Na_3$), provided as 40% by weight aqueous solution, pH: 9.5.

Polymer (B.1): polyethylenimine, density: 1.03 $g/cm^3$, $M_w$: 800 g/mol, $M_n$: 600 g/mol Polymer (B.2): polyacrylic acid, fully neutralized with Na, K-Value according to Fikentscher: 30 in 1 wt-% aqueous solution at a pH value of 7, density: 1.20 $g/cm^3$

EXAMPLE 1

Step (a.1): an aqueous solution of (A.1) was heated to 80° C.

A vessel containing a fluidized bed from 1 kg of solid MGDA-Na$_3$ granule, initial average particle diameter 550 µm, was provided. The fluidization was accomplished by entering a so-called fluidization gas at the bottom of the vessel, said fluidization gas being air with an inlet temperature of 150° C.

As soon as the bed temperature of at least 105° C. was reached, an amount of 2 kg/h of the above aqueous solution of (A.1) was sprayed onto the fluidized bed with the help of a nozzle. The spraying—and thus atomizing—was accomplished with air with a gas inlet temperature of 150° C.

Step (b.1): Every 30 minutes, an aliquot of granule was withdrawn from the vessel through a discharge screw at the side.

Steps (c.1) and (d.1): The aliquot withdrawn in accordance with step (b.1) was classified by sieving in a sieving machine with two sieves, mesh 350 µm and 1,250 µm. Shares of 25% by weight lumps having a minimum diameter of 1,250 µm, and 7% by weight of fines having a maximum diameter of 350 µm were separated off.

Step (e.1): The lumps obtained in step (d.1) were milled down in a hammer mill, type Kinematica Polymix System PM-MFC 90 D. Milled particles with a maximum diameter 500 µm were collected and transferred to step (f).

Step (f.1) The milled lumps obtained in step (e.1) were combined with the fines from step (c.1) and returned portion-wise into the granulator.

A free-flowing granule of (A.1) was obtained that had excellent properties such as, but not limited to excellent percarbonate stability and low hygroscopicity. No hot spots were observed during processing. No sticky material was obtained. A free flowing granule was obtained, and the hygroscopicity was low.

EXAMPLE 2

Basically, example 1 was repeated, with following differences:

In step (a.2), an aqueous solution of (A.1), concentration 40% by weight, and (B.1), 0.25% by weight, was heated to 80° C. and then spray granulated.

In step (c.2), 13% by weight fines were removed. In step (d.2), 28% by weight lumps were removed.

The subsequent steps were repeated mutatis mutandis.

A free-flowing co-granule of (A.1) and (B.1) was obtained that had excellent properties such as, but not limited to excellent percarbonate stability and low hygroscopicity. No hot spots were observed during processing. No sticky material was obtained. The hygroscopicity was low.

EXAMPLE 3

Basically, example 1 was repeated, with following differences:

In step (a.3), an aqueous solution of (A.1), concentration 40% by weight, and (B.1), 10% by weight, was heated to 80° C. and then spray granulated.

In step (c.3), 8% by weight fines were removed. In step (d.3), 26% by weight lumps were removed.

The subsequent steps were repeated mutatis mutandis.

A free-flowing co-granule of (A.1) and (B.1) was obtained that had excellent properties such as, but not limited to excellent percarbonate stability and low hygroscopicity. No hot spots were observed during processing. No sticky material was obtained. The hygroscopicity was low.

EXAMPLE 4

Step (a.4): an aqueous solution of (A.1) was heated to 55° C.

A vessel containing a fluidized bed from 1 kg of solid MGDA-Na$_3$ granule, initial average particle diameter 550 µm, was provided. The fluidization was accomplished by entering a so-called fluidization gas at the bottom of the vessel, said fluidization gas being air with an inlet temperature of 150° C.

As soon as the bed temperature of at least 99° C. was reached, an amount of 2 kg/h of the above aqueous solution of (A.1) was sprayed onto the fluidized bed with the help of a nozzle. The spraying—and thus atomizing—was accomplished with air with a gas inlet temperature of 160° C. and a pressure of 2.8 bar.

Step (b.4): Every 30 minutes, an aliquot of granule was withdrawn from the vessel through a discharge screw at the side. Residual moisture content was 9.5% by weight.

Steps (c.4) and (d.4): The aliquot withdrawn in accordance with step (b.4) was classified by sieving in a continuously operated sieving machine with two sieves, mesh 350 µm and 1,250 µm. Shares of 5% by weight lumps having a minimum diameter of 1,250 µm, and 37% by weight of fines having a maximum diameter of 350 µm were separated off.

Step (e.4): The lumps obtained in step (d.4) were milled down in a bolting machine with 1435 rounds per minute. Milled particles with a maximum diameter 500 µm were collected and transferred to step (f).

Step (f.4) The milled lumps obtained in step (e.4) were combined with the fines from step (c.4) and returned portion-wise into the granulator.

A free-flowing granule of (A.1) was obtained that had excellent properties such as, but not limited to excellent percarbonate stability and low hygroscopicity. No hot spots were observed during processing. No sticky material was obtained. A free flowing granule was obtained, and the hygroscopicity was low.

EXAMPLE 5

Step (a.5): an aqueous solution of (A.1) was heated to 55° C.

A vessel containing a fluidized bed from 1 kg of solid MGDA-Na$_3$ granule, initial average particle diameter 550 µm, was provided. The fluidization was accomplished by entering a so-called fluidization gas at the bottom of the vessel, said fluidization gas being air with an inlet temperature of 150° C.

As soon as the bed temperature of at least 93° C. was reached, an amount of 2 kg/h of the above aqueous solution of (A.1) was sprayed onto the fluidized bed with the help of a nozzle. The spraying—and thus atomizing—was accomplished with air with a gas inlet temperature of 171° C. and a pressure of 3.2 bar.

Step (b.5): Every 30 minutes, an aliquot of granule was withdrawn from the vessel through a discharge screw at the side. Residual moisture content was 11.1% by weight.

Steps (c.5) and (d.5): The aliquot withdrawn in accordance with step (b.5) was classified by sieving in a continuously operated sieving machine with two sieves, mesh 350 µm and 1,250 µm. Shares of 35% by weight lumps having a minimum diameter of 1,250 µm, and 4% by weight of fines having a maximum diameter of 350 µm were separated off.

Step (e.5): The lumps obtained in step (d.5) were milled down in a bolting machine with 1435 rounds per minute. Milled particles with a maximum diameter 500 μm were collected and transferred to step (f).

Step (f.5) The milled lumps obtained in step (e.5) were combined with the fines from step (c.5) and returned portion-wise into the granulator.

A free-flowing granule of (A.1) was obtained that had excellent properties such as, but not limited to excellent percarbonate stability and low hygroscopicity. No hot spots were observed during processing. No sticky material was obtained. A free flowing granule was obtained, and the hygroscopicity was low.

The results are summarized in Table 2.

TABLE 2 process parameters of the exemplified granules

| | fines [wt %] | lumps [wt %] | granule [wt %] | (D50) | % crystallinity |
|---|---|---|---|---|---|
| Experiment 1 | 7 | 25 | 68 | | n.d. |
| Experiment 2 | 13 | 28 | 59 | | n.d. |
| Experiment 3 | 8 | 26 | 66 | | n.d. |
| Experiment 4 | 37 | 5 | 58 | 436 | 80 |
| Experiment 5 | 4 | 35 | 61 | 740 | 86 |

The (D50) refers to the granule.

The invention claimed is:

1. A process for making a powder or granule comprising at least one chelating agent selected from the group consisting of an alkali metal salt of methyl glycine diacetic acid (MGDA), an alkali metal salt of glutamic acid diacetate (GLDA), and an alkali metal salt of iminodisuccinic acid (IDS), wherein the alkali metal salt has a formula selected from the group consisting of formula (I a), (I b) and (I c):

[CH₃—CH(COO)—N(CH₂—COO)₂]M₃₋ₓHₓ    (I a)

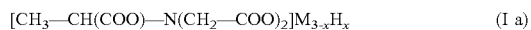

wherein in formula (I a), M is, independently at each occurrence, an alkali metal cation, and x is from zero to 1.0,

[OOC—CH₂CH₂C—CH(COO)—N(CH₂—COO)₂]M₄₋ₓHₓ    (I b)

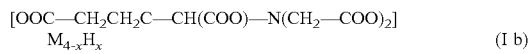

wherein in formula (I b), M is, independently at each occurrence, an alkali metal cation, and x is from zero to 2.0,

[H—N—(CH(COO)—CH₂COO)₂]M₄₋ₓHₓ    (I c)

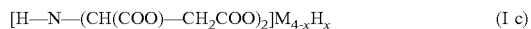

wherein in formula (I c), M is, independently at each occurrence, an alkali metal cation, and x is from zero to 2.0, the process comprising:
  (a) introducing an aqueous solution or aqueous slurry of the chelating agent into a spray-dryer or spray-granulator, and removing most of the water by spray-drying or spray granulation using a gas with an inlet temperature of 125 to 250° C.,
  (b) withdrawing powder or granules, from the spray-dryer or spray-granulator,
  (c) separating off fines from the powder or granules, wherein the fines have a maximum particle diameter of 30 μm in the case of powders and a maximum particle diameter of 350 μm in the case of granules,
  (d) separating off lumps from the powder or granules, wherein the lumps have a particle diameter of 250 μm in the case of powders and 1,000 μm or more in the case of granules, respectively,
  (e) milling the lumps to a maximum particle diameter of 500 μm in the case of granules or to 40 μm in the case of powders, and
  (f) re-introducing the fines from (c) and milled lumps from (e) into the spray-dryer or spray-granulator,
wherein the amount of fines is in a range of from 4 to 18% by total weight of the chelating agent withdrawn in (b), and the amount of milled lumps from (e) is in a range of from 20 to 40% by total weight of the chelating agent withdrawn in (b).

2. The process according to claim 1, wherein in (c) a range of from 80 to 99% by weight of the fines is separated off.

3. The process according to claim 1, wherein the aqueous solution or slurry in (a) comprises at least one (co)polymer (B) selected from the group consisting of homo- and copolymers of (meth)acrylic acid and polyalkylenimines that may be polyalkoyxylated or substituted with carboxymethyl groups.

4. The process according to claim 3, wherein the powder or granule comprises in a range of from 80 to 99.9% by weight of the chelating agent and 0.1 to 20% by weight of the (co)polymer (B), wherein percentages refer to a solids content of the powder or granule.

5. The process according to claim 1, wherein the chelating agent is at least one selected from the group consisting of the trisodium salt of MGDA and the tetrasodium salt of GLDA.

6. The process according to claim 3, wherein the (co)polymer (B) is a per-sodium salt of polyacrylic acid.

7. The process according to claim 3, wherein the (co)polymer (B) is a polyethylenimine that may be polyethoxylated.

8. The process according to claim 3, wherein the (co)polymer (B) has an average molecular weight $M_w$ in a range of from 1,200 to 30,000 g/mol, determined by gel permeation chromatography and referring to the respective free acid.

* * * * *